United States Patent [19]

Dudek

[11] Patent Number: 5,543,114
[45] Date of Patent: Aug. 6, 1996

[54] UNITARY BIOLOGICAL SPECIMEN PROCESSING APPARATUS

[76] Inventor: Peter P. Dudek, Jonstrupvej 269E, Vaerloese, Denmark, DK-3500

[21] Appl. No.: 378,827

[22] Filed: Jan. 27, 1995

[30]    Foreign Application Priority Data

Jan. 31, 1994 [DK]  Denmark .................................. 133/94

[51] Int. Cl.⁶ .................................................. B65D 51/22
[52] U.S. Cl. ........................... 422/102; 422/99; 422/100; 422/104; 220/306; 220/307; 220/339
[58] Field of Search ............................ 422/99, 100, 102, 422/104; 435/299; 220/306, 307, 324, 334, 339

[56]                    References Cited

U.S. PATENT DOCUMENTS

| 4,220,252 | 9/1980  | Beall et al. ................. | 220/307 |
| 4,293,079 | 10/1981 | Lytle ............................. | 220/306 |
| 4,997,100 | 3/1991  | Dudek .......................... | 220/306 |
| 5,080,869 | 1/1992  | McCormick ................. | 422/102 |
| 5,227,137 | 7/1993  | Monti et al. ................. | 422/101 |

FOREIGN PATENT DOCUMENTS

| 0321109 | 10/1988 | European Pat. Off. . |
| 0475496 | 8/1991  | European Pat. Off. . |
| 2580490 | 4/1985  | France . |

*Primary Examiner*—Jill Warden
*Assistant Examiner*—Harold Y. Pyon
*Attorney, Agent, or Firm*—Jacobson, Price, Holman & Stern, PLLC

[57]                        ABSTRACT

A unitary biological specimen processing apparatus has a bottom (1) and a lid (2) for use in the processing multiple tissues of different sizes of biological and medical specimens, such as tissue samples for microscopy, whereby the plate part (15, 18) of the lid (2) and the plate part (14, 17) of the bottom 81) in the apparatus (1, 2) are perforated and in the form of strainers. The apparatus is in its closed position divided by one or more opposing chamber walls (11, 12) into two or more chambers (9, 10) being formed by mating of the opposing chamber walls. The strainer perforations (16, 19) in the plate part (15, 18) of the lid (2) and the plate part (14, 17) of the bottom (2) in a chamber (9, 10) are of the same dimension, and said dimension is different for at least two of the chambers (9, 10). Thereby it is achieved that the number of different apparatuses to be stored for such processings, can be reduced.

3 Claims, 1 Drawing Sheet

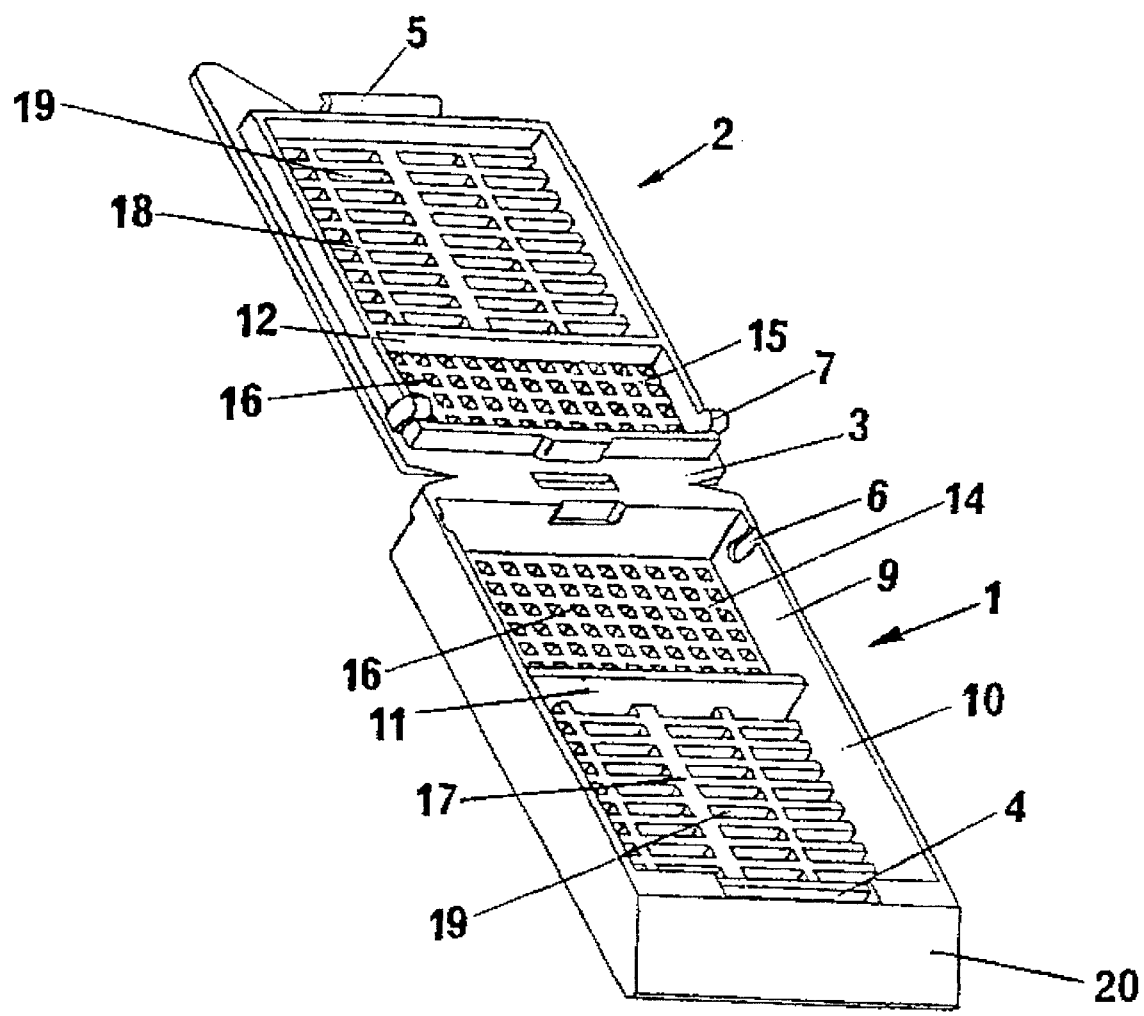

UNITARY BIOLOGICAL SPECIMEN PROCESSING APPARATUS

BACKGROUND AND PRIOR ART

The invention relates to a unitary biological specimen processing apparatus for processing specimens therein, and comprising a rectangular open-topped perforated receptacle member, a cooperable perforated lid, e.g. attached to said receptacle member by a frangible hinge portion, said receptacle member and lid then being capable of relative movement about said hinge portion from a first position permitting placement of specimen in said receptacle member to a second position wherein the open top of said receptacle member is closed by said lid. Such apparatus is e.g. known from EP-patent No. 0 475 496. Hereinafter the receptacle member will be called the bottom and the lid will be called the lid.

The apparatus is for use by the processing of medical specimens or tissue samples for microscopy, whereby the lid and bottom of the apparatus by means of said perforations will have function as strainers.

Such apparatus is used for washing medical specimens having been arranged in the apparatus. The specimens may be samples, such as biopsies, of living tissue, e.g. excidated skin or small samples taken with special hypodermic needles from internal organs for the purpose of making a diagnosis. The specimens should be processed with a number of fluids for making them suitable for microscopy. The tissue samples may be taken in different ways, rendering the specimens different geometrical sizes. The bottom and lid of the apparatus are formed and functions as strainers. A washing fluid can be sent through the one strainer, through the space in the apparatus and out through the second strainer. The perforations of the strainer should be large enough to secure an efficient washing of the specimens, however so small that the specimens in the apparatus cannot be flushed out through the perforations. Thus, there is a need for a number of differently dimensioned strainers and thus a need for a corresponding number of different types of apparatuses.

After a complete processing of a specimen the lid is completely removed from the bottom, the bottom is held over a cup, the bottom is turned upside down so that the specimen falls to the lowermost part of the cup. Subsequently, the bottom is arranged over the specimen which is now covered with a layer of melted wax being poured through the strainer in the bottom of the apparatus, from which it flows over the specimen. The bottom of the apparatus is left on top of the liquid wax. When the wax has hardened to a plug, said plug is removed from the cup. The plug is now fastened to the apparatus which may now be used as support for the plug, while a sharp knife of a microtome can cut thin slices of those parts of the plug containing the specimen to be placed under the microscope. The sides of the bottom can be used for written or printed notes characterizing the specimen.

Thus, one apparatus with a given dimension of strainer perforations are required for each dimension of specimens. Therefore, there must be stored a number of apparatus types corresponding to the number of different dimensions of the strainer perforations needed.

It is the purpose of the present invention to limit the number of different apparatuses to be stored.

Said purpose is achieved by a apparatus of the kind mentioned initially being characterized in that the apparatus by one or more partition walls is divided into two or more mutually separated partitions or compartments, that the strainer perforations, i.e. in the perforations in the lid and bottom of a partition having the same dimension, and that said dimension is in the least different for two of the partitions in the apparatus.

The dimensions of the strainer perforations in each partition are adapted so that they are so much smaller than the dimensions of the specific specimens to be washed in the partition, that the specimens cannot pass the strainer perforations of the partition during the washing. Thus, the apparatus will always have a partition which can be used for washing a specific specimen. Thus, the purpose aimed at is achieved, i.e. a limitation of the number of different apparatuses to be stored. Furthermore, it is achieved that two or more different sized specimens can be washed simultaneously.

The bottom and the lid of the apparatus may preferably, but not necessarily, be mutually connected by a hinge.

However, if hingedly connected it is achieved that the bottom and the lid will not be exchanged by mistake with parts from other apparatuses, and they will always be available and ready simultaneously. Furthermore, it is secured that the correct strainer size in the lid is used for each partition in the apparatus.

Furthermore, the strainer perforations of the smallest dimension may preferably be arranged in that partition of the apparatus being closest to the hinge.

If the lid in the closed condition of the apparatus for some reason should be slightly open and thus provide a leak, said leak would increase functionally with the distance from the hinge. Consequently, a risk of specimens of the smallest dimension being flushed out through a leak is minimal if such specimens are arranged in the partition closest to the hinge, and said partition having strainer perforations with the smallest dimension.

Furthermore, the apparatus according to the invention may preferably be provided with conical strainer perforations being divergent outwardly from the inner of the apparatus.

Thus it is achieved that impurities being washed and rinsed out from the specimens, are not wedged in by the strainer perforation surfaces, and thus there is less risk of one or more specimens having to be rejected because the strainer perforations became blocked and clogged up, and/or the apparatus being rejected and a new washing having to be made, possibly with new specimens.

The invention will now be described in more detail with reference to the drawing showing an embodiment of the apparatus according to the invention, whereby the bottom contains a partition wall dividing the apparatus into two partitions with corresponding equally dimensioned strainer perforations, which in first partition has a square cross section, each with a given size, and in the second partition having a rectangular cross section, each having a substantially larger size, the smallest dimension of which is larger than the largest dimension of the strainer perforations in the first partition.

DESCRIPTION OF THE DRAWINGS

FIG. 1 is an isometric view of the apparatus of the invention in a opened position.

The drawing shows a apparatus with a bottom 1 and a lid 2 made of e.g. plastic and in one piece. The zone in which a side of the bottom 1 and the lid 2 abut each other, forms a hinge 3. The ends of the bottom 1 and the lid 2 opposite to the hinge 3 is shown provided with spring lock parts 4, 5. Close to the hinge 3 the bottom 1 and the lid 2 are provided with other snap engagement parts 6, 7. Said snap engagement parts 6, 7 are designed to enter into function if the hinge 3 should fail.

The inner of the apparatus has been divided into two partitions 9, 10 by a partition wall consisting of two partition wall parts 11, 12, of which the one partition wall part 11 is arranged in the bottom 1 and the second partition wall part 12 in the lid 2 in such a way that the two partition wall parts 11, 12 together form one partition wall when the bottom 1 is closed by the lid 2.

In the first chamber or partition 9 closest to the hinge 3 the plate part 14 of the bottom 1 and plate part 15 of the lid have been provided with strainer perforations 16 of square cross section. In the second partition 10 the plate part 17 of the bottom 1 and the plate part 18 of the lid 2 have strainer perforations 19 with an rectangular cross section. The apparatus can be used for washing either a specimen, the size of which fits into the first partition 9, or another specimen, the size of which fits into the strainer size of the second partition 10. Thus, only apparatuses of one type have to be stored in order to process specimens, each of which needing its own strainer perforation size, in order to be efficiently washed without being flushed out through a strainer perforation.

After the washing process the lid 2 is removed from the bottom along its hinge 3, and the remaining part of the processing is done as already described.

The partition wall between the partitions is preferably split up and has one part in the lid and the other part in the bottom of the apparatus. The space between the two wall parts could very well be insignificant, but at the most of a size corresponding to the smallest strainer perforation size of the adjacent partitions. Thus, the washing effect is increased without the risk of the washed tissue parts being flushed into a neighbouring partition.

I claim:

1. A unitary biological specimen processing apparatus with a bottom and a lid for use in processing multiple tissues of different sizes of biological or medical specimens for microscopy, whereby the plate part of the lid and the plate part of the bottom in the apparatus are perforated and in the form of strainers, and the apparatus in its closed condition is divided by one or more opposing chamber walls on said bottom and lid providing at least two mutually separated chambers formed by mating of said opposing chamber walls; wherein the strainer perforations in one of the mutually separated chambers is a different dimension to the strainer perforations in the other mutually separated chamber and the strainer perforations in the plate part of the lid and the plate part of the bottom in each chamber are of the same dimension.

2. Apparatus according to claim 1, wherein the bottom and the lid of the apparatus are mutually connected by means of a hinge.

3. Apparatus according to claim 1, wherein the strainer perforations having the smallest dimension are arranged in the plate part of the lid and the plate part of the bottom in the chamber closest to the hinge in case the bottom and the lid are connected by a hinge.

* * * * *